United States Patent
Ghahramani et al.

(10) Patent No.: US 6,340,714 B1
(45) Date of Patent: Jan. 22, 2002

(54) CHLORIDE-SENSITIVE ELECTRODE MEMBRANE

(75) Inventors: Massoud Ghahramani, Semriach; Helmut Offenbacher; Christoph Ritter, both of Graz, all of (AT)

(73) Assignee: F. Hoffmann-La Roche AG, Basel (CH)

(*) Notice: Subject to any disclaimer, the term of this patent is extended or adjusted under 35 U.S.C. 154(b) by 0 days.

(21) Appl. No.: 09/661,381

(22) Filed: Sep. 13, 2000

(30) Foreign Application Priority Data

Sep. 13, 1999 (AT) .......................... A 1571/99

(51) Int. Cl.$^7$ ................................ C08J 5/22
(52) U.S. Cl. .................. 521/88; 521/28; 521/34; 521/27; 428/413
(58) Field of Search .............. 521/27, 28, 34, 521/88

(56) References Cited

U.S. PATENT DOCUMENTS

| | | | |
|---|---|---|---|
| 4,144,889 A | * 3/1979 | Tyers et al. | 128/418 |
| 4,629,744 A | * 12/1986 | Uematsu et al. | 521/62 |
| 5,482,855 A | * 1/1996 | Yamafuji et al. | 435/287.1 |
| 5,589,554 A | * 12/1996 | Hiraoka | 525/530 |

FOREIGN PATENT DOCUMENTS

| | | |
|---|---|---|
| AT | 380741 | 6/1986 |
| EP | 0289753 | 11/1988 |
| EP | 0189741 | 9/1990 |

OTHER PUBLICATIONS

Abstract of JP 4–332861 to K. Yamashita entitled "Chlorine Ion Selective Electrode and Field Effect Transistor," Nov. 1992.

\* cited by examiner

Primary Examiner—James J. Seidleck
Assistant Examiner—Melanie D. Bagwell
(74) Attorney, Agent, or Firm—Dykema Gossett PLLC

(57) ABSTRACT

A membrane for use in chloride-sensitive electrodes, comprises a polymer matrix with at least one electroactive component. The polymer matrix of the membrane contains an epoxy resin with an amino compound as a curing agent. For the purpose of reducing the danger of contamination and improving the useful life of the electrode, the epoxy resin is provided with at least one epoxy resin compatible flexibilizer, and the content of epoxy resin plus added flexibilizer in the electrode membrane amounts to more than 60% by weight, while that of the electroactive component is not more than 35% by weight, and preferably not more than 30% by weight.

14 Claims, 2 Drawing Sheets

CHLORIDE-SENSITIVE ELECTRODE MEMBRANE

BACKGROUND OF THE INVENTION

The invention relates to a chloride-sensitive electrode membrane comprising a polymer matrix with at least one electroactive component, the polymer matrix containing an epoxy resin with an amino compound as a curing agent.

DESCRIPTION OF PRIOR ART

Such membranes are used with chloride-sensitive electrodes to determine the chloride concentration in aqueous media, for example.

Chloride electrodes are important in clinical chemistry, above all for diagnostic purposes. Among the anions which are routinely analysed in biological fluids chloride plays a dominant role as the anion which is present at a concentration of 0.1 mol/l in extracellular fluid and hence in blood serum.

For the sensitive element of such membrane electrodes a number of variants are known in the art. Proposals include polypyrrole membranes, for instance (Analyst, October 88/Vol 113, pp 1525), or metalloporphyrins as sensitive components (Helv. Chim. Acta Vol 69, 1986, pp 849). In practical use, however, these compounds have not met with success, and chloride-sensitive electrodes normally use electrochemical sensors whose sensitive component essentially is a mixture of polyvinylchloride (PVC) and an ion exchanger and any further additives required.

The main concern with all of the above electrode membranes is to achieve the highest possible degree of selectivity as regards interfering substances. In this context an ion-sensitive, and especially a chloride-sensitive membrane electrode is proposed in EP 0 189 741 B1, and AT 380 741 B, respectively, in which at least one electroactive component is incorporated in an unplasticized polymer matrix. The content of the electroactive component in the membrane is very high, amounting to 50–90% by weight, and preferably to 60–80% by weight. The polymer matrix is predominantly made of PVC. As an electroactive component methyltridodecyl ammonium chloride is used. Due to the use of extremely large quantities of ion exchanger a very high degree of chloride selectivity is obtained with such membrane electrodes. As a consequence a relatively hydrophilic membrane is obtained which will exhibit a high chloride-selectivity for the conditions prevailing in blood, serum, plasma, or urine due to the validity of the Hofmeister series, such that the membrane will be ideally suited for use in clinical applications. Such membrane electrodes have one major disadvantage, however. Because of the high concentration of the ion exchanger and the high charge density in the membrane resulting there from, the surface of the membrane is extremely prone to the formation of deposits, such as protein deposits. This implies that a membrane electrode in service must be cleansed of biological deposits after every 70–100 readings. This is costly and time-consuming, especially if sample throughput rates are high.

In this context an electrode membrane is referred to, the preparation of which is described in U.S. Pat. No. 4,629,744. The polymer matrix of the membrane is made from a mixture of an epoxy resin and vinyl chloride at a ratio of 8:1 to 1:2 by weight. The mixture further contains one or several solvents, and up to 30% by weight of a quaternary ammonium salt as a selective component, and a curing agent for the epoxy resin. The mixture is put in a shallow dish where the solvent(s) will evaporate, and is allowed to cure at 45° C. for 20 days or longer in order to form a membrane.

In EP 0 289 753 A2, which is also concerned with a chloride-sensitive electrode membrane and is based on prior art according to U.S. Patent No. 4,629,744, it is proposed that no solvents should be used in order to improve membrane properties and that the percentage of PVC and quaternary ammonium salts should be increased. The new membrane composition using 30–50% by weight epoxy resin with triethylene tetramine as a curing agent, and polyvinyl chloride, and up to 30% by weight of a quaternary ammonium salt, is designed to eliminate the drawbacks of the membrane disclosed in U.S. Patent No. 4,629,744, above all its complex manufacturing process and restricted useful life.

The sensor membrane described in EP 0 289 753 is partly successful in this respect, its improved lifetime reaching 4 months, within which the steepness of the sensor characteristic will drop to 70% of the initial value, however. The special membrane composition absolutely demands a certain percentage of PVC to be used in the electrode membrane (32% by weight in the example given), in order to obtain a low membrane resistance desirable for measuring purposes.

SUMMARY OF THE INVENTION

It is an object of this invention to propose a chloride-sensitive electrode membrane which is easy to produce and has a significantly reduced proneness to biological deposits, especially protein deposits, exhibiting a high degree of selectivity in addition to featuring a long useful life while maintaining the initial steepness of its characteristic.

According to the invention this object is achieved by providing that the epoxy resin have at least one epoxy resin compatible flexibilizer, and that the content of epoxy resin plus flexibilizer in the electrode membrane amount to more than 60% by weight, while that of the electroactive component be not more than 35% by weight, and preferably not more than 30% by weight.

Reducing the content of the electroactive component to not more than 30–35% by weight, which is significant when compared to EP 0 189 741 B1, will first of all lead to a significant reduction in charge density, which will have a decisive influence on the membrane's proneness to contamination, and most of all its tendency to protein deposits. This measure by itself would negatively affect the selectivity in conventional PVC electrodes (see FIG. 1). For this reason reducing the concentration of the electroactive component is accompanied by replacing the PVC matrix to a large extent by an epoxy resin with an amino compound as a curing agent, which latter serves as electroactive component.

Unlike in EP 0 289 753 A2, an epoxy resin with a flexibilizer is used in our case, together with an electrode membrane that is essentially free from PVC or contains only a small percentage of PVC (<5 to 10 % by weight). Apparently, the flexibilizer is responsible for the low resistance values, which have positive effects on the useful life of the membrane in service.

The amino compound used for curing assumes a function similar to that of the ion exchanger in the electrode membrane. It has been found unexpectedly that such epoxy resins—contrary to common experience with other ion-sensitive electrodes—are perfectly suited for use with chloride and may be used to great advantage. It has come as a surprise that chloride-sensitive membrane electrodes will thus be obtained whose selectivity compares well with that of conventional sensors, while the susceptibility to deposit formation, useful sensor life and stability of the sensor characteristic are significantly improved.

According to the invention <50% propylene glycoldiglycidyl ether or <50% cresyl glycidyl ether may be added to the epoxy resin as flexibilizer.

In an enhanced version of the invention a surplus of amino compound may be provided which should exceed the concentration necessary for curing by 150% at most. The epoxy resin should retain a certain degree of mechanical flexibility after curing, however. This flexibility is mainly required for promoting the mobility of the molecules or ions taking part in the measuring process in the potentiometric sensor.

To further increase the selectivity of the electrode membrane the electroactive component may at least partially be composed of an ion exchanger, so that both the curing agent and the ion exchanger will serve as selective component. The total concentration of the two substances should be significantly smaller than the concentration of the ion exchanger in the PVC membrane electrode known from EP 0 189 741 B1. In principle, it is possible to produce a chloride-sensitive electrode simply based on an epoxy resin plus flexibilizer and an amino compound as a curing component. The additional use of an ion exchanger will improve membrane selectivity, if a similar or even better response than with known PVC membranes is desired.

Within certain limits the concentration of the curing agent may be used to influence the selectivity of the membrane electrode. The concentration of the curing agent should not be increased arbitrarily, however, to prevent the membrane from becoming brittle or detached from the case or substrate. Advantageously, concentrations of the curing agent should exceed the concentration required for the actual curing process by not more than 150%.

A preferred ion exchanger would be an aliphatic quaternary ammonium compound, and preferably methyltridodecyl ammonium chloride or methyltrioctyl ammonium chloride.

According to the invention the electrode membrane is composed of about 80 percent by weight epoxy resin plus flexibilizer, and about 10±2 percent by weight curing agent, and about 10±3 percent by weight methyl tridodecyl ammonium chloride, for example.

In a variant of the invention the electrode membrane is composed of about 70 percent by weight epoxy resin plus flexibilizer, and 10±2 percent by weight curing agent, and about 20±3 percent by weight methyltrioctyl ammonium chloride (contained, for instance, in Aliquat® 336 by FLUKA, Buchs, Switzerland; order # 91042). For both variants the epoxy resin CY 208 (modified epoxy resin containing ≦50% propylene glycoldiglycidyl ether as flexibilizer) and the curing agent HY 951 by CIBA GEIGY may be used.

BRIEF DESCRIPTION OF THE DRAWINGS

The diagram in

DETAILED DESCRIPTION OF THE PREFFERED EMBODIMENTS

Figure 1:
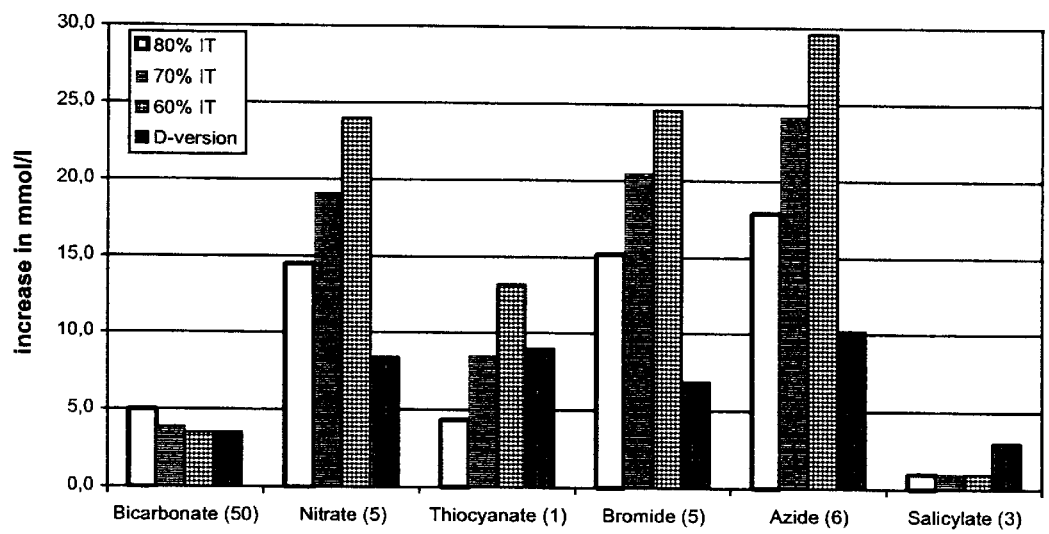
FIG. 1 shows changes in selectivity as a function of ion exchanger content.

The diagram in FIG. 1 presents different interferents (bicarbonate, nitrate, thiocyanate, bromide, azide, and salicylate) and their influence on the measured result (signal increase in mmol/l). The added quantity of interferent in mmol/l is given in the brackets. For measuring, conventional PVC membrane electrodes (as described in EP 0 189 741 B1, for example) were used on the one hand, with varying concentrations of the ion exchanger IT (80% by weight, 70% by weight, 60% by weight), and an electrode membrane according to the invention (D-version) on the other hand. In a conventioanl PVC electrode a reduction of the ion exchanger to 60% by weight is accompanied by a significant deterioration in selectivity, whereas the D-version shows excellent selectivity values for the majority of interferents.

Figure 2:
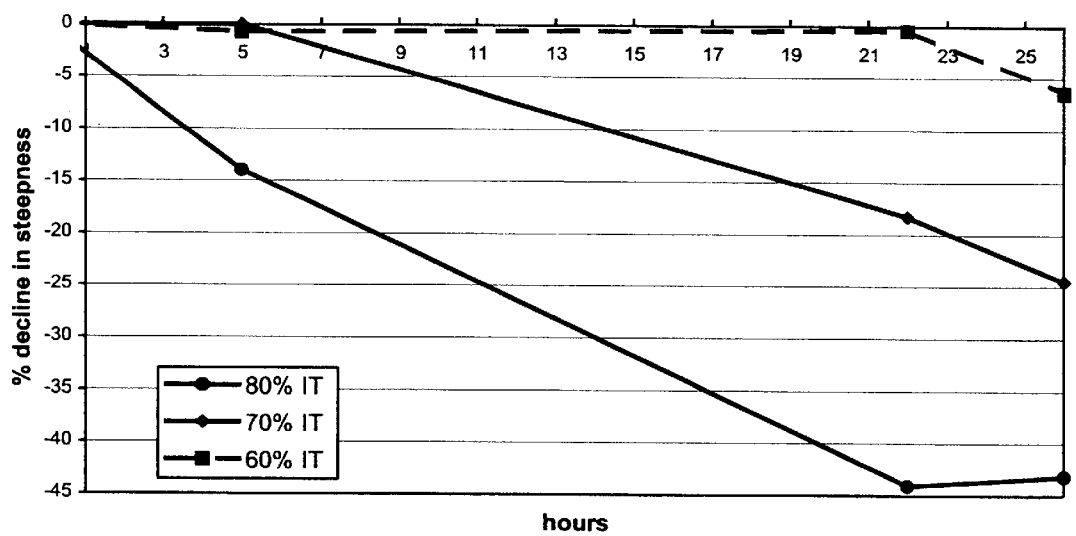
FIG. 2 changes in characteristic steepness due to protein deposits as a function of time in conventional electrode membranes, FIG. 3 changes in characteristic steepness as a function of time in the sensor according to the invention compared to a prior art sensor, and FIG. 4 the stability of a chloride electrode according to the invention, in continual service over 15 weeks.

In FIG. 2 the duration of exposure of a conventional PVC electrode to diluted serum is plotted on the abscissa in hours, versus the decrease in steepness of the electrode characteristic on the ordinate in percent. The bottom curve shows a sensor with high concentration of ion exchanger (IT=80%) and rapid decline in steepness, the topmost curve shows a sensor with low concentration of ion exchanger (IT=60%). This serves as an indicator that the contamination tendency is much smaller for lower ion exchanger concentrations.

Figure 3:
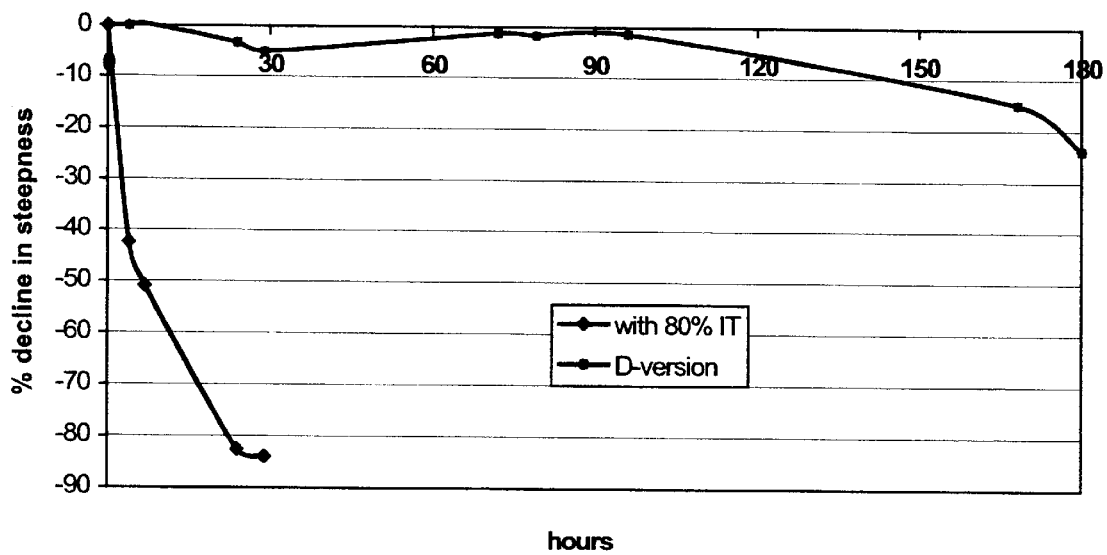

In FIG. 3 the change in steepness is plotted in percent over the duration of serum exposure in hours. The measured curve (D-version) shows the considerably smaller contamination tendency of an electrode membrane according to the invention compared to a conventional PVC membrane (with 80% IT).

Figure 4:
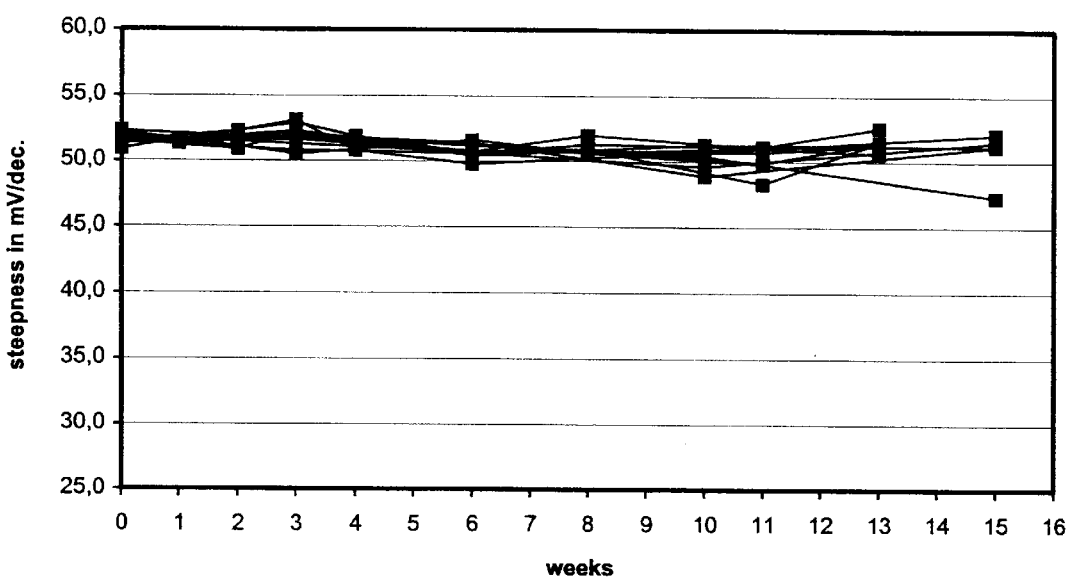

In FIG. 4 the stability of cloride-sensitive electrode membranes according to the invention is indicated by the steepness of the electrode characteristic (mV/dec) as a function of time (weeks). Within a period of 15 weeks the steepness of the characteristic is very stable for all electrode membranes measured, tests taking place at 40° C. and a total of more than 120 hours of serum contact. Both the high measuring temperature and the contact with serum (serum diluted with water at a ratio of 1:9) represent extreme measuring conditions. It has been found unexpectedly that the forming of deposits of biological materials on the membrane, i.e., the membrane's contamination tendency, is significantly increased for serum samples diluted 1:9 compared with undiluted samples. During the 15 weeks measuring period simulating normal operating conditions the electrode membranes were washed several times with a cleaning fluid to remove protein deposits. This did not result in any changes in membrane composition leading to a decline in electrode steepness.

In selecting the ion exchanger for use with an electrode membrane according to the invention it is essential that the ion exchanger should be compatible with the polymer matrix. In this context the use of shorter chain aliphatic ion exchangers has been found in some instances to be preferable to those with longer chains. As regards Aliquat® (basically a methyl trioctyl ammonium chloride), for example, 50% by weight and more may be incorporated into certain epoxy resins (such as CY 208 made by CIBA GEIGY), provided that the increased contamination tendency of the membrane is found acceptable; if methyltridodecyl ammonium chloride is used, only somewhat more than 10% by weight may be incorporated into these epoxy resins.

With the electrode membrane proposed by the invention good measured results will be obtained with serum and blood samples while its tendency to contamination remains low. In addition, a high degree of selectivity is ensured, even in comparison with conventional PVC membrane electrodes (see AT-B 380 741, for example), as is shown in the table below.

TABLE 1

| Interferent | Concentration of interferents (mmol/l) | Signal change AT-B 380741 (mmol/l) | Signal change invention (mmol/l) |
|---|---|---|---|
| Bromide | 5 | 16 | 7 |
| Nitrate | 5 | 14 | 8 |
| Rhodanide | 1 | 22 | 6 |
| Salicylate | 5 | 2 | 3 |

In the instance of heavy sample exposure the membrane should be treated from time to time with suitable cleaning agents. It has been found that such cleansing may be accompanied by a temporary increase in the membrane's sensitivity to salicylate, which may be a nuisance. For a remedy the invention proposes that the side of the electrode membrane in contact with the sample should be coated with a cover film, preferably of modified polyurethane.

What is claimed is:

1. A chloride-sensitive electrode membrane comprising a polymer matrix with at least one electroactive component, said polymer matrix containing an epoxy resin with an amino compound as a curing agent, wherein said epoxy resin is provided with at least one epoxy resin compatible flexibilizer from a group consisting of propylene glycol diglycidyl ether and cresyl glycidyl ether, and wherein the content of said epoxy resin plus said flexibilizer in said electrode membrane amounts to more than 60% by weight, while that of said electroactive component is not more than 35% by weight.

2. A chloride-sensitive electrode membrane according to claim 1, comprising not more than 30% by weight of electroactive component.

3. A chloride-sensitive electrode membrane according to claim 1, comprising a surplus of said amino compound which will exceed a concentration necessary for curing by up to 150%.

4. A chloride-sensitive electrode membrane according to claim 1, wherein said electroactive component is at least partially composed of an ion exchanger.

5. A chloride-sensitive electrode membrane according to claim 4, wherein said ion exchanger is an aliphatic quaternary ammonium compound.

6. A chloride-sensitive electrode membrane according to claim 5, wherein said ion exchanger is methyltridodecyl ammonium chloride.

7. A chloride-sensitive electrode membrane according to claim 5, wherein said ion exchanger is methyl-trioctyl ammonium chloride.

8. A chloride-sensitive electrode membrane according to claim 1, wherein said epoxy resin is provided with $\leq 50\%$ of said flexibilizer.

9. A chloride-sensitive electrode membrane according to claim 1, wherein said electrode membrane is free of PVC.

10. A chloride-sensitive electrode membrane according to claim 1, wherein said electrode membrane contains a percentage of <5 to 10% by weight PVC.

11. A chloride-sensitive electrode membrane according to claim 6, wherein said electrode membrane is composed of about 80% by weight epoxy resin plus flexibilizer, and about 10±2% by weight curing agent, and about 10±3% by weight methyltridodecyl ammonium chloride.

12. A chloride-sensitive electrode membrane according to claim 7, wherein said electrode membrane is composed of about 70% by weight epoxy resin plus flexibilizer, and 10±2% by weight curing agent, and about 20±3% by weight methyltrioctyl ammonium chloride.

13. A chloride-sensitive electrode membrane according to claim 1, wherein one side of said electrode membrane is in contact with a sample and is coated with a cover film.

14. A chloride-sensitive electrode membrane according to claim 13, wherein said cover film comprises polyurethane.

* * * * *